(12) United States Patent
Er et al.

(10) Patent No.: US 6,374,139 B1
(45) Date of Patent: Apr. 16, 2002

(54) METHOD AND APPARATUS FOR IMPLEMENTING OPERATING CHANGES AND DISPLAYING OPERATING CHANGE INFORMATION FOR AN IMPLANTABLE MEDICAL DEVICE

(75) Inventors: Siew Bee Er, Newhall; Quang Ly, Rosemead, both of CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/400,756

(22) Filed: Sep. 22, 1999

Related U.S. Application Data

(62) Division of application No. 08/995,783, filed on Dec. 22, 1997, now Pat. No. 6,101,415.

(51) Int. Cl.⁷ .................................................. A61N 1/37
(52) U.S. Cl. ........................................................ 607/27
(58) Field of Search .............................. 607/27, 28, 29

(56) References Cited

U.S. PATENT DOCUMENTS

| | | | |
|---|---|---|---|
| 4,601,291 A | * | 7/1986 | Boute et al. ................ 128/419 |
| 4,791,936 A | | 12/1988 | Snell et al. |
| 4,809,697 A | | 3/1989 | Causey et al. |
| 4,940,052 A | | 7/1990 | Mann et al. |
| 4,944,298 A | | 7/1990 | Sholder |
| 4,944,299 A | | 7/1990 | Silvian |
| 5,285,792 A | * | 2/1994 | Sjoquist et al. ............. 128/697 |
| 5,292,341 A | | 3/1994 | Snell |
| 5,309,919 A | | 5/1994 | Snell et al. |
| 5,423,867 A | | 6/1995 | Poore et al. |
| 5,431,691 A | | 7/1995 | Snell et al. |
| 5,487,754 A | * | 1/1996 | Snell et al. ................... 607/27 |
| 5,487,755 A | * | 1/1996 | Snell et al. ................... 607/27 |

* cited by examiner

*Primary Examiner*—William E. Kamm

(57) ABSTRACT

An implantable medical device, such as a pacemaker, stores information pertaining to a variety of events detected and/or triggered by the medical device for subsequent transmission to an external programmer device. The external programmer device displays graphical representations of the information under the control of a physician operating the programmer device. Examples of information stored by the pacemaker include information pertaining to operations triggered within the pacemaker as a result of the condition of the patient, such as an auto-mode switching event automatically triggered as a result of conditions detected within the heart, or as a result of the condition of the pacemaker itself, such as a battery test operation. Still other examples of information recorded by the pacemaker include information pertaining to programmer operations triggered by a remote programmer device, such as a heart base rate programming operation triggered by an external programmer.

17 Claims, 6 Drawing Sheets

METHOD AND APPARATUS FOR IMPLEMENTING OPERATING CHANGES AND DISPLAYING OPERATING CHANGE INFORMATION FOR AN IMPLANTABLE MEDICAL DEVICE

This application is a divisional of application Ser. No. 08/995,783 filed on Dec. 22, 1997, now U.S. Pat. No. 6,101,415.

FIELD OF THE INVENTION

The invention generally relates to implantable medical devices and to external programmer devices used in connection therewith and in particular to methods and apparatus for processing information within an external programmer device pertaining to events recorded by the implantable medical device.

BACKGROUND OF THE INVENTION

A wide range of implantable medical devices are provided for surgical implantation into humans or animals. One common example is the cardiac pacemaker. Another is the implantable cardioverter defibrillator. Other examples include devices for stimulating or sensing portions of the brain, spinal cord, muscles, bones, nerves, glands or other body organs or tissues.

Implantable medical devices, particularly pacemakers, are often configured to be used in conjunction with an external programmer device which allows a physician to program the operation of the pacemaker to, for example, control the specific parameters by which the pacemaker detects arrhythmia conditions and responds thereto. For instance, the external programmer may allow the physician to specify the sensitivity with which the pacemaker senses electrical signals within the heart and to further specify the amount of electrical energy to be employed for pacing the heart in circumstances where expected heart signals are not sensed. Additionally, the external programmer may be configured to receive and display a wide variety of diagnostic information detected by the pacemaker, such as the electrical heart signals sensed by the pacemaker and the responsive pacing signals.

With regards to the display of diagnostic information, many pacemakers operate only in real time to detect electrical activity in the heart as it occurs and to transmit data pertinent thereto to the external programmer for immediately display. In other words, no capability is provided within the pacemaker for storing sensed signals for later transmission to the external programmer. Hence, diagnostic information can only be retrieved and displayed for signals sensed by the pacemaker while the external programmer is currently communicating with the pacemaker, which is typically only while the patient in which the pacemaker is implanted is in a hospital or within a physician's office. With such systems, only very limited information, if any, can be stored by the pacemaker for subsequent transmission to the external programmer.

U.S. Pat. No. 5,431,691 to Snell et al. entitled "Method and System for Recording and Displaying a Sequential Series of Pacing Events", however, provides a system employing a pacemaker and an external programmer wherein the pacemaker continuously records diagnostic data pertaining to the condition of the heart of the patient for subsequent transmission to the external programmer. The data is stored within circular buffers within the pacemaker configured to ensure that, if the buffers become full, newly recorded data overwrites the oldest previously recorded data. The recorded data is ultimately transmitted to the external programmer which is configured to provide a wide variety of different displays of the data to assist the physician in analyzing the condition of the heart and rendering appropriate diagnoses. Hence a significant improvement is achieved over previous systems that were not capable of storing diagnostic data for subsequent processing and display but were instead only capable of displaying information pertaining to the current condition of the heart. U.S. Pat. No. 5,431,691 to Snell et al. is incorporated by reference herein.

The system of Snell et al. processes and records the diagnostic data in an "event record" format which allows the data to be efficiently stored, accessed and displayed. Specific types of diagnostic data processed by the system of Snell et al. are listed in TABLE I.

TABLE I

| EVENT NAME | EVENT TYPE |
|---|---|
| AV | A-pulse followed by a V-pulse |
| AR | A-pulse followed by an R-wave |
| PVE | Premature ventricular event |
| PV | P-wave followed by a V-pulse |
| PR | P-wave followed by an R-wave |
| P @ MTR-V | P-wave at maximum tracking rate followed by a V-pulse |
| P @ MTR-R | P-wave at maximum tracking rate followed by a R-wave |
| MAGNET | Magnet placed over the implanted device-either singly or in combination with an external telemetry system |

As can be seen from TABLE I, the events processed by the system of the Snell et al. patent are primarily events sensed within the heart of the patient. Event records containing information pertaining to those events are recorded within the pacemaker for subsequent transmission to the external programmer for display thereon in a variety of formats including event record displays, event bar graphs, rate bar graphs, rate time graphs, and event time graphs, each under the control of the physician operating the external programmer. More specifically, the event record display presents the various detected events of TABLE I and the corresponding pacing rate with respect to the time of the occurrence of the event. For periods of time while then pacemaker is in a dual-chamber mode (such as DDD, DDI etc.), the events presented include PV, PR, AV (or V when the mode is VDDR or VDD), AR and PVC (premature ventricular contraction). For periods of time while the pacemaker is in a single-chamber mode (such as VVI, AAI etc.), the events are presented merely as paced or sensed. The event bar graph presents a histogram of different event types listing the total number of counts of each event type for a selected period of time. The event time graph presents histograms of event types vs. time of event occurrence. The rate bar graph presents histograms of sensed and paced events vs. their rate. The rate time graph presents histograms of rates vs. times. Further information regarding the different displays may be found in the Snell et al. patent.

As can be appreciated a wide range of useful information, particularly directed to events sensed within the heart, is thereby provided to assist the physician in rendering a diagnosis as to any arrhythmia or other condition the patient may exhibit or to assist the physician in making choices as to adjusting various parameters by which the pacemaker monitors and paces the heart. The information is displayed in a variety of convenient graphical formats to help the physician visualize the information quickly and easily to facilitate prompt and accurate diagnoses.

Although the system of the Snell et al. patent represents a significant improvement over previous systems, room for further improvement remains. In particular, it would be desirable to provide a system capable of recording and displaying further diagnostic data pertaining to events in addition to those which are listed in TABLE I including, for example, diagnostic data pertaining to: events detected within the heart during refractory periods following stimulation pulses; operational events triggered within the pacemaker as a result of the condition of the patient (such as an automode switching event); and operational events triggered within the pacemaker as a result of the condition of the pacemaker itself (such as battery tests or lead fault detection tests). It is to these ends that aspects of the invention are primarily directed.

SUMMARY OF THE INVENTION

In accordance with one aspect of the invention, a system is provided for detecting and displaying information received from an implantable medical device capable of generating a stimulation signal within tissue connected to the implantable medical device and capable of sensing electrical events occurring within the tissue. The system comprises means for receiving signals from the implantable medical device representative of events detected during a refractory period following generation of a stimulation signal and means for graphically displaying icons representative of the events detected during the refractory period.

In one specific example, the implantable medical device is a pacemaker and the system for detecting and displaying information is an external programmer device separate from the pacemaker. The events detected during the refractory period include the detection of: a) a P-wave during a relative Post-Ventricular Atrial Refractory Period (PVARP) not followed by a ventricular pulse; b) an R-wave during a relative Ventricular Refractory Period; or c) a P-wave during an Atrial Refractory Period during an AV/PV interval. The means for graphically displaying the detected events is a computer display screen or a computer print-out device.

In accordance with another aspect of the invention, a system is provided for detecting and displaying information received from an implantable medical device capable of being programmed by signals received from a remote programming device. The system comprises means for receiving signals from the implantable medical device representative of programming operations triggered within the implantable medical device by the signals received from the remote programming device and means for graphically displaying icons representative of the programming operations triggered within the implantable medical device.

In one specific example, wherein the implantable medical device includes a pacemaker, the programming operations triggered within the pacemaker are selected from a group consisting of pacemaker mode selection, heart base rate selection, heart rest rate selection, maximum pacemaker tracking rate selection, maximum pacemaker sensing rate selection and pacemaker rate responsive AV/PV delay selection. The remote programming device may be a magnet operated by a physician or may be part of a programmer unit operated by a physician.

In accordance with yet another aspect of the invention, a system is provided for detecting and displaying information received from an implantable medical device that is capable of triggering internal operations based upon sensed conditions. The system comprises means for receiving signals from the implantable medical device representative of operations triggered by the implantable medical device in response to conditions sensed within the implantable medical device and means for graphically displaying icons representative of the operations triggered within the implantable medical device.

In one example, wherein the implantable medical device includes a pacemaker, the pacemaker is capable of sensing conditions of the heart of a patient in which the pacemaker is implanted. The aforementioned operations are triggered based upon the sensed conditions of the heart and include operations such as automatic pacemaker mode switching (i.e. automode switching), pacemaker mediated tachycardia (PMT) detection, premature ventricular contraction (PVC) detection, and a pacemaker rate hysteresis search.

In another example, wherein the implantable medical device again includes a pacemaker, the pacemaker is capable of sensing performance parameters representative of its own performance. The operations triggered within the pacemaker are triggered based upon the sensed performance parameters and include operations such as a battery test and a lead fault detection test.

Hence, with the invention, systems are provided for graphically displaying a wide variety of diagnostic information not heretofore easily available to the physician, to thereby assist the physician in making quick and informed decisions regarding, for example, the patient's condition or the condition of the implantable medical device.

Other objects and advantages of the invention are provided as well. Method embodiments of the invention are also provided.

BRIEF DESCRIPTION OF THE INVENTION

DETAILED DESCRIPTION OF THE INVENTION

Figure 1:
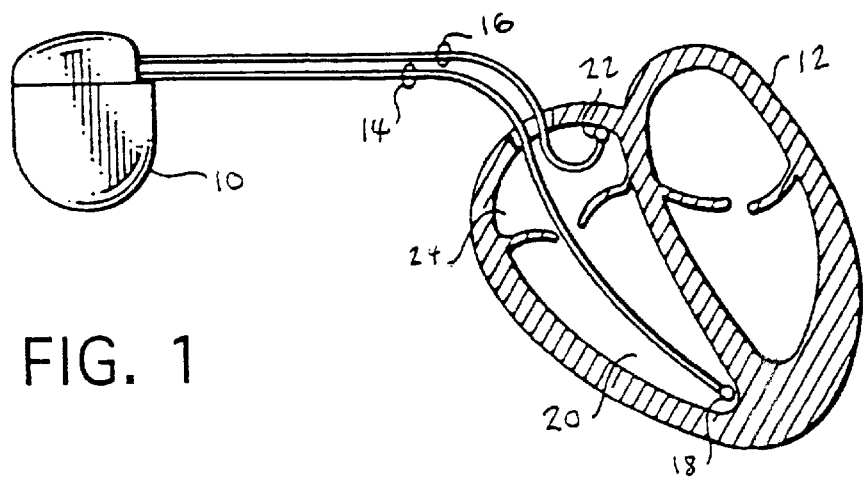
FIG. 1 shows an implantable pacemaker coupled to a heart via a pair of electrical leads.

The invention relates to improved techniques for providing information to a physician regarding the events detected by an implantable medical device. The invention will be described primarily with reference to a pacemaker used in conjunction with an external programmer device, but principles of the invention are applicable to other implantable medical devices or other external devices as well.

The Figures illustrate a pacemaker/programmer system having a pacemaker for implantation into a patient and an external programmer for programming the operation of the pacemaker and for processing and displaying information received from the pacemaker regarding the condition of a patient in which the pacemaker is implanted and regarding the condition of the pacemaker itself. The information is stored within the pacemaker in an event record format which efficiently allows a wide variety of types of information to be stored, along with the date and time at which the information was stored, within the pacemaker for subsequent transmission to the external programmer. The external programmer includes processing units for receiving event records transmitted by the pacemaker and for generating a wide variety of graphical displays of the information contained within the event records under the control of the physician operating the external programmer.

The Snell et al. patent, incorporated by reference above, describes a predecessor pacemaker/programmer system which also operates to generate, store and process certain types of information within event records to generate certain displays based upon the information contained within the event records. The pacemaker/programmer system of the present invention operates to generate, store and process many additional types of information within event records to generate enhanced displays based upon the information contained within the event records. In the following descriptions, for the sake of clarity in describing pertinent features of the enhanced pacemaker/programmer system of the present invention, many details of the operation of the overall pacemaker/programmer system provided in the Snell et al. patent are not repeat herein. Additional operational details pertaining to either the pacemaker, programmer or both may be found in the following patents, each of which is also incorporated by reference herein: U.S. Pat. No. 4,940,052 entitled "Microprocessor controlled rate-responsive pacemaker having automatic rate response threshold adjustment"; U.S. Pat. No. 4,809,697 entitled "Interactive Programming And Diagnostic System For Use With Implantable Pacemaker"; U.S. Pat. No. 4,791,936 entitled "Apparatus For Interpreting And Displaying Cardiac Events Of A Heart Connected To A Cardiac Pacing Means"; U.S. Pat. No. 5,309,919 entitled "Method And System For Recording, Reporting, And Displaying The Distribution Of Pacing Events Over Time And For Using Same To Optimize Programming"; U.S. Pat. No. 4,944,299 entitled "High Speed Digital Telemetry System For Implantable Device"; U.S. Pat. No. 5,292,341 entitled "Method And System For Determining And Automatically Adjusting The Sensor Parameters Of A Rate-Responsive Pacemaker"; U.S. Pat. No. 5,423,867 entitled "Rate-Responsive Pacemaker Having Automatic Sensor Threshold With Programmable Offset"; and U.S. Pat. No. 4,944,298 entitled "Atrial Rate Based Programmable Pacemaker With Automatic Mode Switching Means".

FIG. 1 illustrates an implantable pacemaker 10 coupled to a heart 12 by way of a ventricular lead 14 and an atrial lead 16. Ventricular lead 14 includes an electrode 18 positioned in the right ventricle 20 of the heart and atrial lead includes an electrode 22 positioned in the right atrium 24 of the heart.

Various internal components of the pacemaker operate to sense the electrical activity of the heart, such as the presence of P-waves and R-waves, using electrodes 18 and 22 and to selectively stimulate the heart in response to events sensed within the heart by conducting electrical stimulation pulses to the heart using the electrodes. The pacemaker may be configured to operate in either a single-chamber mode or a dual-chamber mode. Certain of the events sensed within the heart are recorded by internal components of the pacemaker within event records for subsequent transmission to an external programmer (FIG. 2) for display thereon in a graphical format. TABLE II provides a list of sensed events stored in pacemaker 10 of FIG. 1 using event records while the pacemaker is operating in the dual-chamber mode. Notably, the events listed in TABLE II include three events $P_{REF}$ detected, $R_{REF}$ detected and $P_{AV}$ detected occurring during refractory periods following the generation of stimulation signals.

TABLE II

| SENSED EVENT NAME | SENSED EVENT TYPE |
|---|---|
| AV | A-Pulse Followed By A V-Pulse Detected |
| AR | A-Pulse Followed By An R-Wave Detected |
| PVE | Premature Ventricular Event Detected |
| PV | P-Wave Followed By A V-Pulse Detected |
| PR | P-Wave Followed By An R-Wave Detected |
| P @ MTR-V | P-Wave At Maximum Tracking Rate Followed By A V-Pulse Detected |
| P@ MTR-R | P-Wave At Maximum Tracking Rate Followed By A R-Wave Detected |
| $P_{REF}$ | P-Wave Detected During A Relative Post-Ventricular Atrial Refractory Period (PVARP) Not Followed By A Ventricular Pulse |
| $R_{REF}$ | R-Wave Detected During A Relative Ventricular Refractory Period |
| $P_{AV}$ | P-Wave Detected During An Atrial Refractory Period During An AV/PV Interval |
| $P_{REF}R$ | P-Wave In PVARP Followed By Sensed Inhibiting R-Wave |
| ActAV | Activity Sensor Driven Atrial Pulse Followed By A Ventricular Pulse |
| ActAV | Activity Sensor Driven Atrial Pulse Followed By Inhibiting R-Wave |

For periods of time when the pacemaker is operating in the single-chamber mode, the pacemaker stores paced, sensed, $P_{REF}$ and $R_{REF}$ events, rather than all of the events of TABLE II.

Other internal components of pacemaker 10 of FIG. 1 operate to receive programming signals from an external programmer (FIG. 2) and to modify the operation of the pacemaker in accordance with the programming signals. Each time the pacemaker receives programming signals, the pacemaker records a record of the corresponding "programming event" as an event record for subsequent transmission to the external programmer for display thereon in a graphical format. TABLE III provides a list of programming events stored by the pacemaker 10 of FIG. 1.

TABLE III

| PROGRAMMING EVENT NAME | PROGRAMMING EVENT TYPE |
|---|---|
| Mode | Pacemaker Mode Programmed |
| Base Rate | Heart Base Rate Programmed |
| Rest Rate | Heart Rest Rate Programmed |
| Maximum Tracking Rate | Maximum Pacemaker Tracking Rate Programmed |
| Maximum Sensor Rate | Maximum Pacemaker Sensor Rate Programmed |
| Rate Responsive AV/PV Delay | Rate Responsive AV/PV Delay Programmed |

Still other internal components operate to automatically trigger pacemaker operations based upon the condition of the patient as sensed by the pacemaker. Such "patient condition-triggered events" are also stored within event records for subsequent transmission to, and display on, the external programmer. TABLE IV provides a list of all patient condition-triggered events stored using event records by pacemaker 10.

TABLE IV

| PATIENT-CONDITION TRIGGERED EVENT NAME | PATIENT-CONDITION TRIGGERED EVENT TYPE |
|---|---|
| Auto-mode Switching | Pacemaker Mode Automatically Switched |
| PMT Detection | Pacemaker Mediated Tachycardia (PMT) Detected |
| PVC Detection | Premature Ventricular Contraction (PVC) Detected |
| Rate Hysteresis | Rate Hysteresis Search Performed |

Still other internal components operate to automatically trigger pacemaker operations based upon the condition of the pacemaker itself, such as a battery test operation triggered in response to the detection of a low battery voltage. A record of such "pacemaker condition-triggered events" are also stored within event records. TABLE V provides a list of all patient condition-triggered events stored using event records by pacemaker 10.

TABLE V

| PACEMAKER-CONDITION TRIGGERED EVENT NAME | PACEMAKER-CONDITION TRIGGERED EVENT TYPE |
|---|---|
| Battery Test | Battery Voltage Test Performed |
| VARIO Test | Minimum Capture Test Performed |
| Diagnostic Data Suspension | Diagnostic Data Suspended |
| Lead Supervision | Lead Fault Detection Test Performed |
| RRT Test | Recommended Replacement Time (RRT) Battery Test Performed |

Thus TABLES II–V list exemplary events stored by the pacemaker of the presently-described exemplary embodiment of the invention within event records. In other embodiments, not all of the events listed in the TABLES may be recorded. In still other embodiments, additional events may also be recorded. As can be appreciated, a wide range of variations are permissible within the scope of the invention.

As noted, the various event records are stored within the pacemaker for subsequent transmission to, and display using, the programmer (FIG. 2) within a graphical display format. Alternatively, if the external programmer is currently in communication with the pacemaker, the event records may be immediately transmitted to the programmer as they are recorded.

The specific format with which the different types of events are stored and otherwise processed differ somewhat depending upon the type of event. In particular, the sensed events listed in TABLE II may be stored in a different format from the various operational events listed in Tables III–V. The format for storing the operational events of TABLE III–V is referred to herein as an "event control records". As will be described below, event control records are handled somewhat differently during the generation of some of the displays presented by the external programmer.

Figure 2:
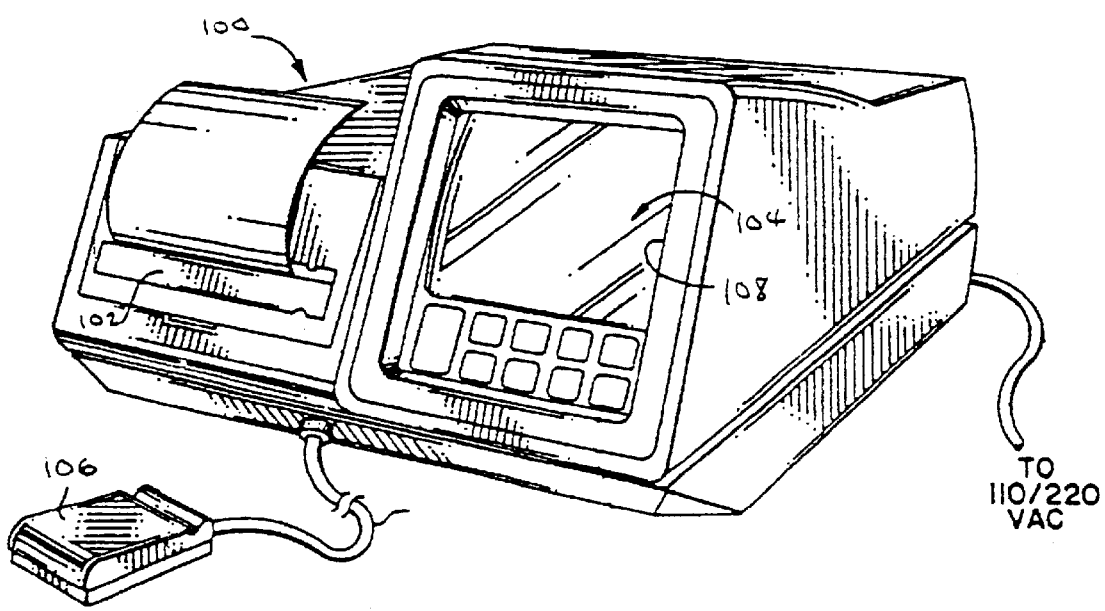
FIG. 2 is a perspective view of an external programmer that may be used for communicating with the implantable pacemaker of FIG. 1.

FIG. 2 illustrates an external programmer 100 configured for receiving the aforementioned event records from pacemaker 10 (FIG. 1) and for generating graphical displays or printouts of the event records. Programmer 100 includes a printer 102 for printing out a graphical representation of the information contained within the event records and a display screen 104 for displaying the graphical representation. Generation of the graphic displays is subject to the control of a physician or other user operating the external programmer. To this end, external programmer 100 presents various menus on display screen 104 for use in controlling operation of the programmer to program pacemaker 10 (FIG. 1) to perform any of the functions listed above in TABLE III. Various menus are also presented on display screen 104 for use in controlling operation of the programmer to generate displays on display screen 104 of information received from the pacemaker including the aforementioned graphical representations of the event records representative of the events listed above in TABLES II–V. Programmer 100 receives menu selections from the physician through a touch screen 108 which overlays display screen 104. Actual programming of the pacemaker is achieved using a telemetry head 106 which, in use, is placed is proximity to the pacemaker.

Figure 3:
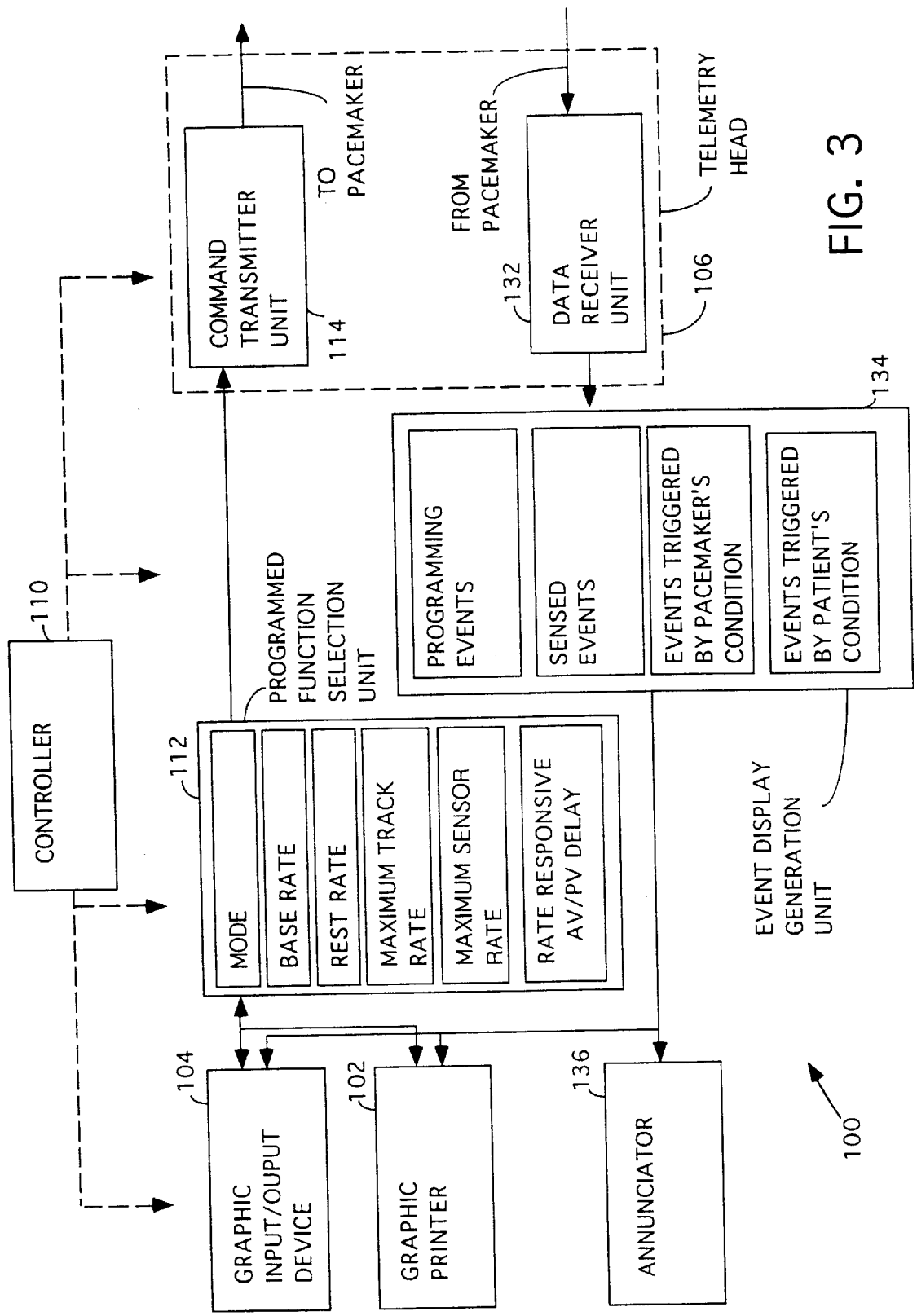
FIG. 3 is block diagram of pertinent components of the external programmer of FIG. 2 for use in generating and displaying enhanced event markers and event control records received from the implantable pacemaker of FIG. 1.
Figure 4:
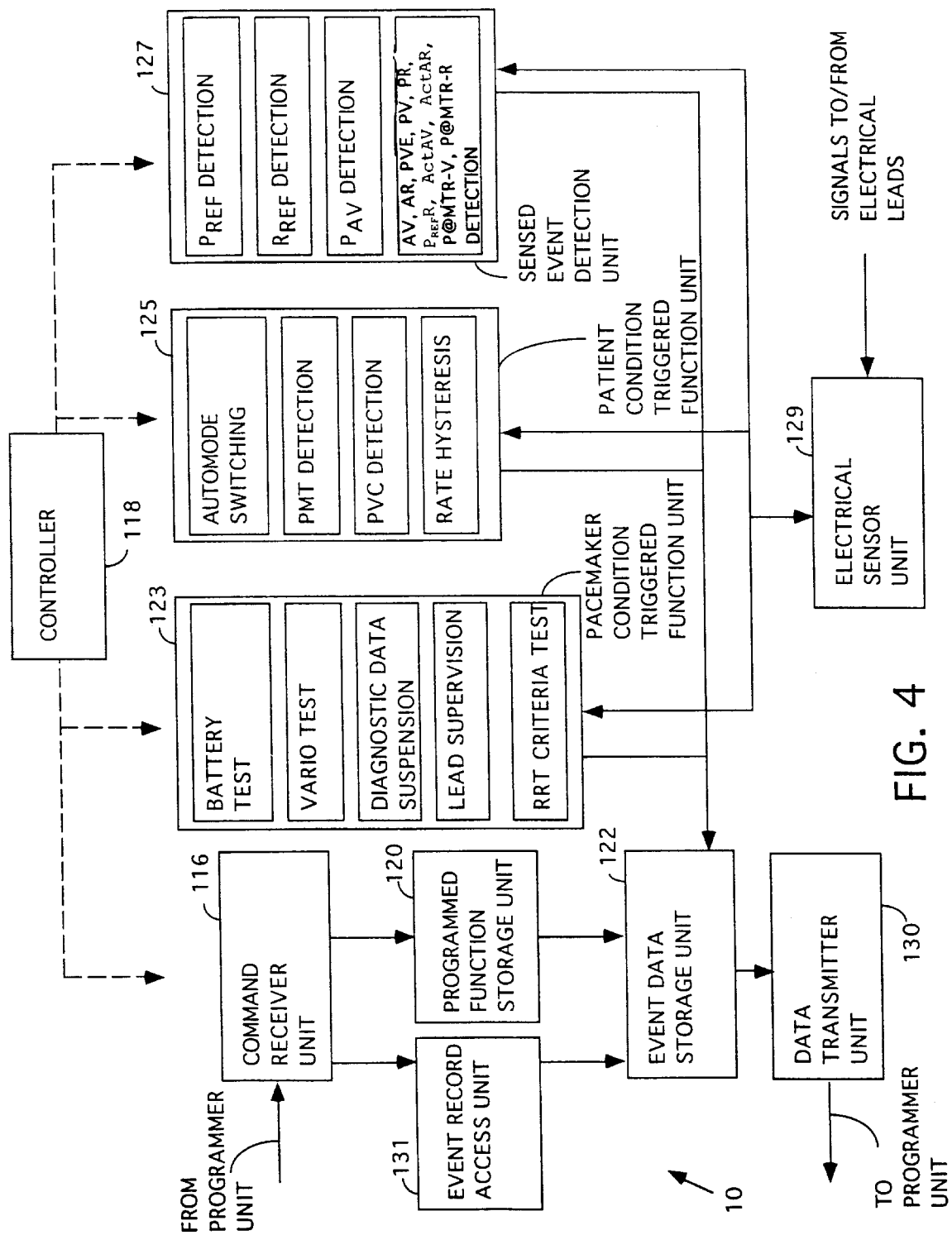
FIG. 4 is block diagram of pertinent components of the implantable pacemaker of FIG. 1 for use in generating the enhanced event markers and event control records for display using the external programmer of FIG. 3.

With reference to FIGS. 3 and 4, internal components of pacemaker 10 and programmer 100 that are pertinent to the processing of event records within the pacemaker and to the generation of event record displays using the external programmer will now be described. Components of programmer 100 are shown in FIG. 3. Components of pacemaker 10 are shown in FIG. 4. Referring first to FIG. 3, a controller 110 of programmer 100 controls graphic display 104 to display the aforementioned menus from which the physician may select, among other options, to program the operation of the pacemaker or to generate graphical displays of the event records previously recorded by the pacemaker.

Assuming first that the physician chooses to program the pacemaker, a program function selection unit 112 controls graphic device 104 to display a list of the programming options corresponding to the programming events listed in TABLE III, i.e. the graphic device displays a list of the following programming options: Mode, Base Rate, Rest Rate, maximum Tracking Rate, Maximum Sensing Rate, and Rate Responsive AV/PV Delay. (Further information regarding these programming options may be found in the above-referenced patents.) The physician selects one or more of the programming options from the list then enters any pertinent parameters, such as the applicable pacemaker mode, rate value or delay value, on one or more display screens (not separately shown) presented by programmed function selection unit 112 using graphical display 104. A command transmitter unit 114 of telemetry head 106 transmits the appropriate command signals to pacemaker 10 to program the pacemaker in the selected manner.

Referring to FIG. 4, the programming signals transmitted by programmer 100 are received by a command receiver unit 116. A controller 118 operates in response to the received commands to program the appropriate pacemaker functional units (not shown) to perform the selected operations in response to the programming signals. Additionally, the programming signals are forwarded by command receiver unit 116 to a programmed function storage unit 120 which stores information pertaining to the received programming command as an event control record (along with the date and time that the command was received) in an event data storage unit 122 to thereby maintain a record of the receipt of the programming signal or subsequent access. Event data storage unit 122 may be a circular buffer configured as described in the Snell et al. patent.

The event data storage unit additionally stores a wide variety of other pacemaker event information including event records corresponding to any of the other events listed within TABLES III–V. To this end, pacemaker 10 additionally includes pacemaker condition-triggered function unit 123, a patient condition-triggered function unit 125 and a sensed event detection unit 127, each of which operates continuously and automatically within the pacemaker (subject to the overall control of controller 118) to detect particular events, trigger responsive operations and record information pertaining to the detected events within event data storage unit 122. The specific information to be recorded along with each event varies depending upon the particular event. For example, for the sensed events of TABLE II, the rate at which the event was detected is stored along with an identification of the type of sensed event. For the events of Tables III–V, the corresponding event control record that is stored includes an identification of the type of event and any additional pertinent information. For example, for an automode switching event, the event control records stored additionally contains an identification of the previous pacemaker mode and the new pacemaker mode. For a battery test event, the event control record additionally stores an indication of whether the battery failed the test.

Now the purpose of the various functional units of the pacemaker of FIG. 4 will be described. Pacemaker condition-triggered function unit 123 continuously monitors the operation of other units of the pacemaker, such as the pacemaker battery (not shown) and triggers appropriate operations in response thereto. More specifically, pacemaker condition-triggered function unit 123 triggers a battery test, a VARIO test, a lead supervision test and an RRT criteria test. The battery test is periodically performed to determine if the battery has sufficient power by, for example, determining if the battery voltage has fallen below a predetermined minimum threshold and, if so, appropriate warning signals are generated. Also, the pacemaker may modify its own operations, perhaps to suspend further diagnostic data acquisition to save battery power. The VARIO test is a minimum capture test performed to determine the minimum voltage of a stimulation pulses sufficient to be captured and responded to by the heart. Typically, the voltage level for stimulation pulses is then set based upon the minimum capture threshold to ensure that a minimum amount of energy is used in each stimulation pulse while still ensuring adequate capture of the pulse. The lead fault detection test (also referred to a Lead Supervision test) is periodically performed to test the integrity of the electrical leads (FIG. 1) perhaps by sensing the impedance thereof. The recommended replacement time (RRT) test is periodically performed to determine if the battery, or other power source of the pacemaker, should be replaced and, if so, appropriate warning signals are generated. The RRT test differs from the previously-described battery test in that a more sophisticated set of tests are performed. Additionally, pacemaker condition-triggered function unit 123 may selectively suspend the further acquisition of diagnostic data. This is typically done if the battery begins to lose power. By suspending diagnostic data acquisition, a greater amount of remaining battery power is thereby preserved for sensing and pacing the heart.

Each time an operation is triggered by pacemaker condition-triggered function unit 123, the unit also operates to store an event control record within data storage unit 122 representative of the triggered event. Accordingly, each of the events listed in TABLE III, above, may be recorded within the data storage unit.

Patient condition-triggered function unit 125 continuously monitors the status of the patient's heart via an electrical sensor unit 129 connected to leads 14 and 16 (FIG. 1) and triggers appropriate operations in response to certain detected conditions. More specifically, patient condition-triggered function unit 125 triggers automode switching, PMT detection, PVC detection and a rate hysteresis operation. Automode switching is performed to automatically switch the pacing mode of the heart to, for example, switch from a dual mode to a single chamber mode. PMT detection is performed continuously to detect a pacemaker mediated tachycardia such as an endless loop tachycardia, a tracking atrial fibrillation. PMT is also referred to as pacemaker reentry tachycardia, circus tachycardia or endless loop tachycardia. If PMT is detected, appropriate responsive therapy is automatically performed by the pacemaker in an attempt to terminate the PMT. For example, atrial sensing may be terminated via an automode switching operation. PVC detection is performed continuously to detect premature ventricular contractions (i.e. ventricular contractions occurring during a pre-defined refractory period). The physician may elect to shorten the refractory period to ensure that PVC pulses are properly sensed. Proper sensing of PVC's may be helpful in eliminating or preventing PMT's. The rate hysteresis search is performed periodically to set the hysteresis escape rate. The hysteresis escape rate is typically set to a value less than the base rate to inhibit pulse generation in some circumstances to allow the heart further time to generate its own pulse.

Each time an operation is triggered by patient condition-triggered function unit 125, the unit also operates to store an event control record within data storage unit 122 representative of the triggered event. Accordingly, each of the events listed in TABLE IV, above, may be recorded within the data storage unit.

Sensed event detection unit 127 continuously monitors the signals received from the patient's heart to detect selected events and records pertinent information pertaining to the events within the data storage unit. More specifically, sensed event detection unit 127 detects each of the events listed in TABLE II. The last three events, namely $P_{REF}$, $R_{REF}$ and $P_{AV}$, are events occurring during a refractory period following generation of a stimulation pulse. Knowledge of these refractory events is helpful to the physician in setting refractory periods and the like.

Thus while pacemaker 10 of FIG. 1 is in operation, it continuously monitors various aspect of its condition and the condition of the patient in which it is implanted and stores appropriate diagnostic information as event records in event data storage unit 122. Additionally, as noted above, the pacemaker may receive programming commands which are also stored in the data storage unit.

Ultimately, the physician may wish to display diagnostic information pertaining to any of the events previously recorded. Such may be desirable during a follow-up session with the patient in which the pacemaker is implanted. To display the diagnostic information, the physician then selects for the display of recorded events (by using appropriate menus not separately shown herein displayed by graphic device 104 of FIG. 3). Controller 110 forwards appropriate event record retrieval commands to pacemaker 10 (FIG. 4) via command transmitter unit 114 of telemetry head 106. The retrieval commands are received by command receiver unit 116 of the pacemaker of FIG. 4 and forwarded to an event record access unit 131 which retrieves all stored event records from event data storage unit 122 for transmission to the programmer via a data transmitter unit 130. The event records are received by a data receiver unit 132 of telemetry head 106 of the programmer of FIG. 3 and forwarded to an event display generation unit 134. The event display generation unit operates to display a representation of the event records using either graphic device 104, printer 102, or both. Additionally, the event display generation unit may trigger an annunciator 136 to generate an audible sound upon the display of certain event records to help direct the physician's attention to the display.

A variety of graphical displays of information contained within the event records may be generated under control of the physician. In the presently described exemplary embodiment, the following graphical displays of information contained within the event records may be displayed under the control of the physician: event record displays, event bar graphs, rate bar graphs, rate time graphs, and event time graphs. The event record display presents the various detected events of Tables II–V and the corresponding pacing rate with respect to the time of the occurrence of the event. Briefly, for periods of time while the pacemaker is in a dual-chamber mode (such as DDD, DDI etc.), the events presented include PV, PR, AV (or V when the mode is VDDR or VDD), AR and PVC (premature ventricular contraction). For periods of time while the pacemaker is in a single-chamber mode (such as VVI, AAI etc.), the events are presented merely as paced or sensed. The event bar graph presents a histogram of different event types listing the percentage of time of each event relative to the total event time. The event time graph presents histograms of event types vs time of event occurrence. The rate bar graph presents histograms of sensed and paced events vs. their rate. The rate time graph presents histograms of rates vs times. In other embodiments, more or fewer displays may be generated. Details of the manner by which the various event record displays are generated are provided in the Snell et al. patent. Accordingly, the following descriptions will be directed primarily to the portions of selected displays containing additional information not provided by the display screens of the Snell et al. patent.

Figure 5:
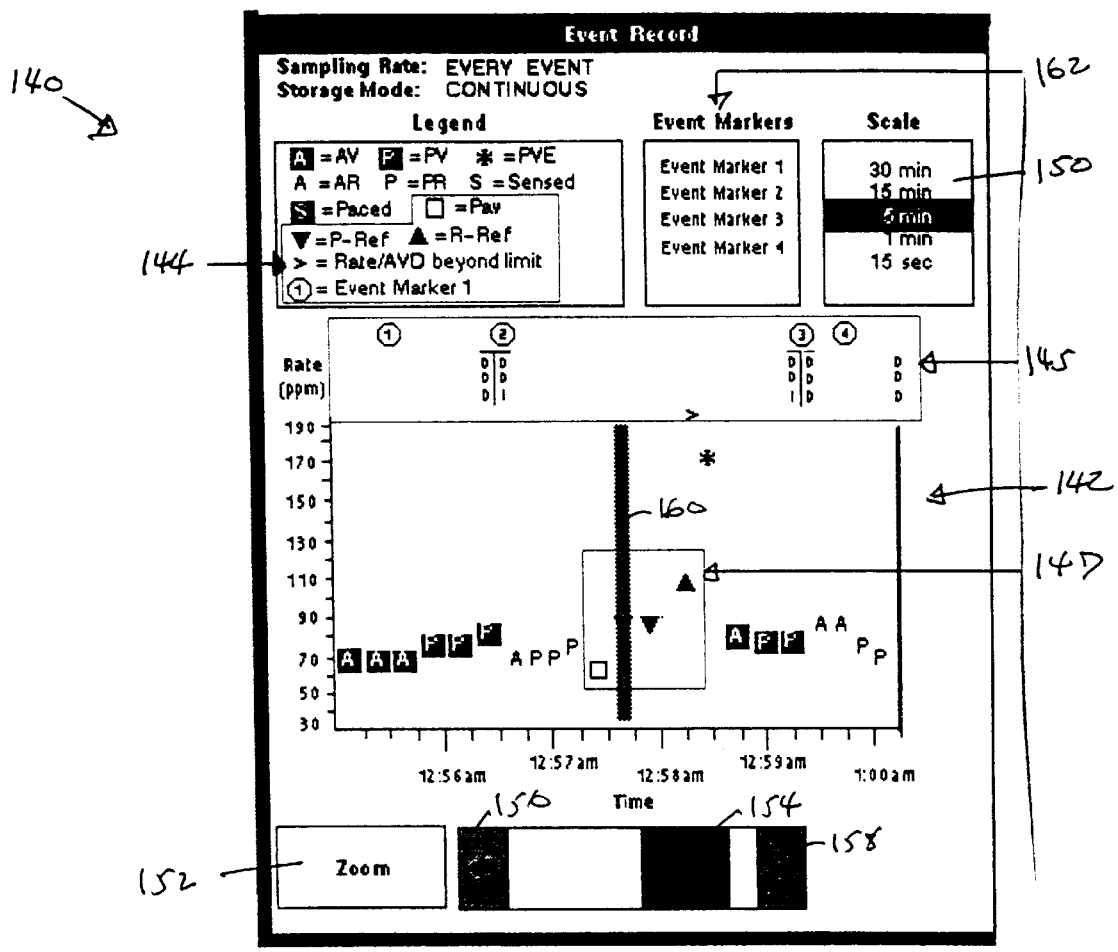
FIG. 5 is an exemplary event record screen displayed by the external programmer device of FIG. 2.

FIG. 5 illustrates an exemplary event record display screen 140 for events recorded during a period of time when the pacemaker was in a dual-chamber mode. The event record display screen includes a graphical display 142 of recorded events shown using various graphical icons distributed along a horizontal time axis and a vertical rate axis. The events displayed may include any of the events listed in the TABLES above. The sensed events of TABLE II are represented each by a unique icon positioned along the time axis of the graphic display at the time at which the event was sensed as recorded within the corresponding event record and positioned along the rate axis at a location representative of the rate at which the event was sensed. In the example of FIG. 5, rates are scaled between 30 and 190 pulses per minute (ppm). Legend 144 provides a summary of the unique graphical icons presented in display 142 such as: an A for an AR event; a P for PR event; a square black box with a reverse video 'A' for an AV event; a square black box with a reverse video 'P' for a PV event; a '★' for a PVE event; a white square box for a $P_{AV}$ event; an upside down black triangle for $P_{REF}$ event; a black triangle for $R_{REF}$ event; etc. All other events (i.e. the events listed in Tables III–V) are identified as 'event markers' and are graphically represented by sequential arabic numerals each within a circle, such as a 1 in a circle. The event markers themselves are displayed along a top portion 145 so graphical display 142 at a point along the time-axis corresponding to the time at which the event was recorded by the pacemaker. The event markers, however, are not scaled along the vertical rate axis. For an automode switching event, in addition to providing an arabic numeral in a circle, the previous and subsequent pacemaker modes are also displayed (e.g. DDD v. DDI).

For data collected during a period of time when the pacemaker was in a single-chamber mode, the event record display shows a solid black square box with a reverse video 's' for a paced event, an 's' for a sensed event, an upside down black triangle for a $P_{REF}$ event and a black triangle for an $R_{REF}$ event In the dual-chamber example of FIG. 5, a variety of AV, PV, AR and PR events are shown, along with four refractory period events 147: one $P_{AV}$ event followed by two $P_{REF}$ events and a single $R_{REF}$ event. The latter $R_{REF}$ event is followed by a star icon indicated the first subsequent sensed event.

The event record display also provides a selectable time scale list 150 to allow the physician to select the time scale over which data is to be displayed within graphical display 142. As shown, exemplary time scales include fifteen seconds, one minute, five minutes, fifteen minutes and thirty minutes. Although not shown, additional time scales include one hours, two hours, five hours, twelve hours, thirty hours, sixty hours, one hundred twenty hours, one week, two weeks, four weeks, eight weeks, sixteen weeks, thirty weeks, and fifty-two weeks. Depending upon the time scale, the event record display may not be able to show all individual events. If so, the event record display presents a compressed display with time slots providing the maximum, minimum and average rates of the events within the time slots.

The event record display also provides a ZOOM button 152 which, upon selection, causes the external programmer to selectively display only a portion of the previous event record display. At that time, the ZOOM button is replaced with an UN-ZOOM button to allow for a return to the previous display. Furthermore, the event record display includes a time bar 154 which graphically indicates the portion of the total amount of event record data received from the pacemaker that is currently displayed. In the example of FIG. 5, only about one third of the total event record data retrieved from the pacemaker is displayed. Selection of one of the arrow buttons 156 and 158 causes the graphical display to be scrolled to the left or right, respectively, to display other portions of the event record data received from the pacemaker. Additionally, a vertical line 160 is displayed to provide a marker to assist the physician in scrolling or otherwise examining data. Although not shown, still other buttons may be presented on the display including, for example, a PRINT button or a CANCEL button.

A selectable event marker list 162 displays a list of the displayed event markers by number. Upon selection of one the events listed in the event marker list, programmer 100 (FIG. 3) generates a pop-up display providing pertinent information pertaining to the selected event marker.

Figure 6:
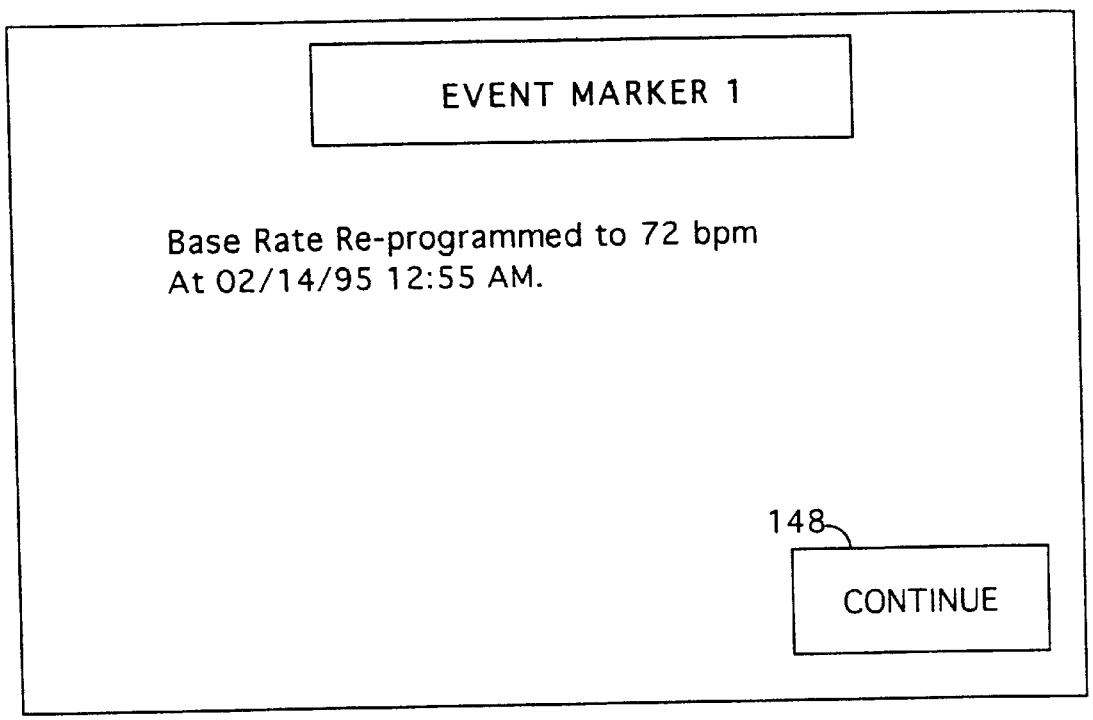
FIG. 6 is an exemplary pop-up display screen displayed by the external programmer device of FIG. 2 providing details of an exemplary programming event that had been recorded by the pacemaker of FIG. 1.

FIG. 6 provides an example of a pop-up display providing information pertaining to one event marker, specifically a "base rate change" programming event recorded by the pacemaker (and identified within FIG. 5 as event marker '1'). As can be seen from FIG. 6, the pop-up display provides a textual description of the base rate programming operation including the new base rate as well as the date and time at which the base rate change occurred. Selection of a CONTINUE button 148 within the pop-op display causes the external programmer to redisplay the event record display of FIG. 5 to allow for selection of another event marker for generation of another pop-up display or for selection of any other appropriate function.

For each different event marker, different information may be provided within the pop-up display. Generally speaking, all pertinent information stored as part of the event control record is displayed. Thus, for example, in the pop-up display generated from a battery test event marker, the pop-up display indicates whether the battery failed the test and additionally displays the date and time. Additional diagnostic information may be presented as well. For example, for a pop-up display generated from an RRT. test event marker wherein the recommended replacement has been reached, the following information is presented along with the date and time of the RRT:

"Pulse generator has reached RRT for the following possible reasons:

1. Battery is RRT;
2. Battery is near RRT.
3. RRT Triggered because of high output pacing
4. RRT was possibly triggered by applied defibrillator/discharge
5. RRT could have been triggered by implantable defibrillator."

Figure 7:
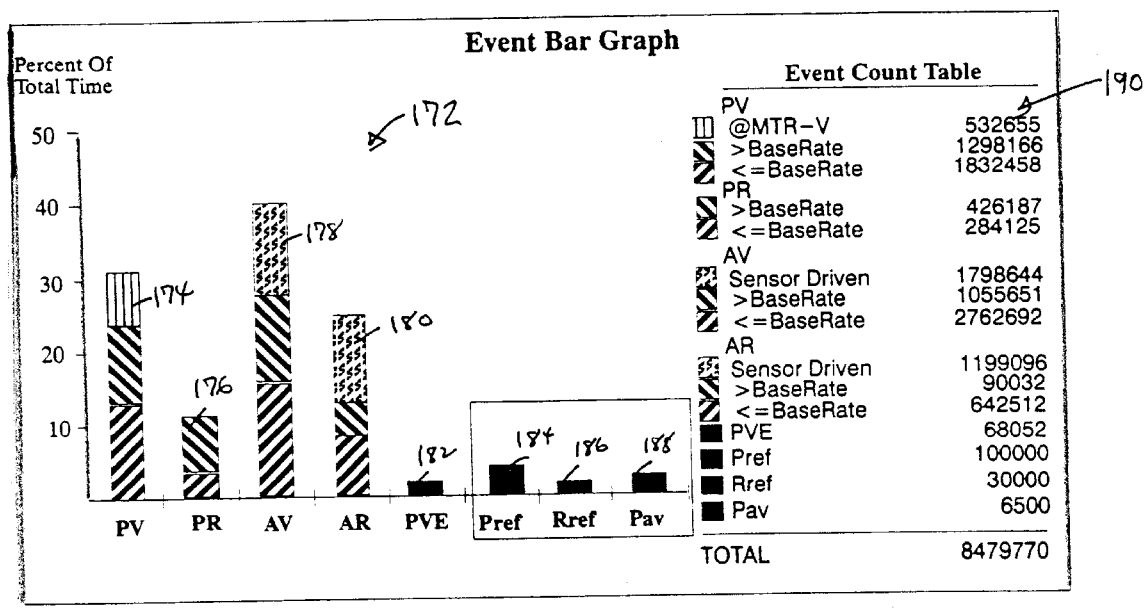
FIG. 7 is an exemplary event bar graph display screen displayed by the external programmer device of FIG. 2.

Referring to FIG. 7, an exemplary event bar graph display 170 is shown having a bar graph 172 providing a set of bars each separately corresponding to one of the sensed events listed in TABLE II, namely PV, PR, AV, AR, PVE and the three refractory period events $P_{REF}$, $R_{REF}$ and $P_{AV}$. The bars are distributed along a vertical axis of the bar graph and extend upwardly along a vertical axis representative of "Percentage of Total Time". Each of the bars for the PV, PR, AV, AR events are sub-divided into different sections. More specifically, a PV 174 bar is split into three sections to show the relative percentages of data collected either @MTR-V, above the base rate or below the base rate. A PR bar 176 is split into two sections to show the relative percentages of data collected either above the base rate or below the base rate. An AV bar 178 is split into three sections to show the relative percentages of data either sensor driven, collected above the base rate or collected below the base rate. An AR bar 180 is also split into three sections to show the relative percentages of data either sensor driven, collected above the base rate or collected below the base rate. The remaining bars: a PVE bar 182, a $P_{REF}$ bar 184, a $R_{REF}$ bar 186, and a $P_{AV}$ bar 188 are not individually sub-divided. An event count table 190 is also provided which lists the actual numerical counts of each category of event shown in the event bar graph. For event records recorded during periods of time when the pacemaker was in a single-chamber mode, the event histogram includes only histogram bars for sensed, paced, $P_{REF}$ and $R_{REF}$.

Thus a few exemplary displays of the event record data have been-specifically illustrated. Additionally, a variety of other displays are generated by the exemplary embodiment of the invention including the aforementioned event bar graphs, rate bar graphs, rate time graphs, and event time graphs, which each provide different graphical representations of the sensed events of TABLE II. Additionally details regarding the characteristics of those displays are provided in the Snell et al. patent. Of course, it should be understood, that in the exemplary embodiment herein described, each of those displays is modified as appropriate to additionally incorporate the refractory period events $P_{REF}$, $R_{REF}$ and $P_{AV}$. Also, it should be noted that a wide variety of other types of displays of the event records may alternatively be generated in accordance with the principles of the invention. For example, a graphical display may be generated that merely provides a list of all of the event records along with the date and time at which the events were recorded, perhaps arranged in chronological order.

Eventually, the physician terminates the presentation of graphical representations of the event records by selecting an appropriate menu option, such as a CANCEL menu option (not shown), and can thereafter select other programmer operations.

What has been described are systems for generating, storing, processing and graphically displaying a wide variety of information pertaining to events detected by a pacemaker. The various functional components of the exemplary system may be implemented using any appropriate technology including, for example, microprocessors running software programs or application specific integrated circuits (ASIC'S) executing hard-wired logic operations. Although described with respect to a pacemaker used in conjunction with an external programmer, aspects of the invention are applicable to other system, such as systems employing other implantable medical devices or systems employing other types of external interfaces for use with the implantable device. The exemplary embodiments of the invention described herein are merely illustrative of the invention and should not be construed as limiting the scope of the invention.

What is claimed is:

1. A system for detecting and displaying information received from an implantable medical device that is capable of triggering operating changes based upon sensed conditions, said system comprising:

means for receiving signals from the implantable medical device representative of the operating changes triggered within the implantable medical device; and means for graphically displaying icons representative of the operating changes triggered within the implantable medical device.

2. The system of claim 1, wherein the operating changes represented are selected from a group consisting of pacemaker auto-mode switching, pacemaker mediated tachycardia (PMT) detection, premature ventricular contraction (PVC) detection, and a pacemaker rate hysteresis search.

3. The system of claim 1, wherein the operating changes are selected from a group consisting of a battery test, a minimum capture test, the suspension of the acquisition of diagnostic data, a lead fault detection test, and a recommended battery replacement time test.

4. The system of claim 1, wherein the means for graphically displaying the icons comprises a computer display screen.

5. The system of claim 1, wherein the means for graphically displaying the icons comprises a computer print-out device.

6. A method for detecting and displaying information using an implantable medical device and an external display device, said method comprising the steps of:

sensing conditions using the implantable medical device;

triggering operating changes within the implantable medical device in response to the sensed conditions;

transmitting signals, from the implantable medical device to the external display device, representative of operating changes triggered within the implantable medical device in response to the sensed conditions;

receiving the transmitted signals at the external display device; and graphically displaying icons on the external display device representative of the operating changes that had been triggered within the implantable medical device.

7. The method of claim 6, wherein the step of sensing conditions using the implantable medical device includes the step of sensing conditions within a patient in which the medical device is implanted.

8. The method of claim 7, wherein the implantable medical device includes a pacemaker and wherein the step of triggering operating changes includes the step of selecting from a group consisting of performing pacemaker auto-mode switching, detecting pacemaker mediated tachycardia (PMT), detecting premature ventricular contraction (PVC), and performing a pacemaker rate hysteresis search.

9. The method of claim 6, wherein the step of sensing conditions using the implantable medical device includes the step of sensing parameters representative of its own performance.

10. The method of claim 9, wherein the implantable medical device includes a pacemaker and wherein the step of triggering operating changes within the implantable medical device includes the step of selecting from a group consisting of performing a battery test, performing a minimum capture test, suspending the acquisition of diagnostic data, performing a lead fault detection test, and performing a recommended battery replacement time test.

11. A system for detecting and displaying information, comprising:
   an implantable medical device that is operative to trigger operating changes based upon sensed conditions and to generate corresponding signals representative of the operating changes; and
   an external display device that is operative to receive the signals from the implantable medical device, wherein the external display device is further operative to process the signals and to graphically display icons representative of the operating changes.

12. The system of claim 11, the implantable medical device is capable of sensing conditions of a patient in which the medical device is implanted and wherein the operating changes are triggered based upon the conditions of the patient.

13. The system of claim 12, wherein the implantable medical device comprises a pacemaker and wherein the operating changes represented are selected from a group consisting of pacemaker auto-mode switching, pacemaker mediated tachycardia (PMT) detection, premature ventricular contraction (PVC) detection, and a pacemaker rate hysteresis search.

14. The system of claim 11, wherein the implantable medical device is capable of sensing performance parameters representative of its own performance and wherein the operating changes are triggered based upon the sensed performance parameters.

15. The system of claim 14, wherein the implantable medical device comprises a pacemaker and wherein the operating changes are selected from a group consisting of a battery test, a minimum capture test, the suspension of the acquisition of diagnostic data, a lead fault detection test, and a recommended battery replacement time test.

16. The system of claim 11, wherein the external display device comprises a computer display screen.

17. The system of claim 11, wherein the external display device comprises a computer print-out device.

* * * * *